US012384817B2

(12) United States Patent
Chung et al.

(10) Patent No.: US 12,384,817 B2
(45) Date of Patent: Aug. 12, 2025

(54) PEPTIDE HAVING PROTECTIVE ACTIVITY AGAINST CELL DAMAGE CAUSED BY PARTICULATE MATTER, AND USES FOR SAME

(71) Applicant: CAREGEN CO., LTD., Gyeonggi-do (KR)

(72) Inventors: Yong Ji Chung, Gyeonggi-do (KR); Eun Mi Kim, Gyeonggi-do (KR); Eung Ji Lee, Gyeonggi-do (KR); Han A Kang, Gyeonggi-do (KR); Bo Byeol Hwang, Gyeonggi-do (KR)

(73) Assignee: CAREGEN CO., LTD., Gyeonggi-Do (KR)

( * ) Notice: Subject to any disclaimer, the term of this patent is extended or adjusted under 35 U.S.C. 154(b) by 342 days.

(21) Appl. No.: 18/038,871

(22) PCT Filed: Nov. 26, 2020

(86) PCT No.: PCT/KR2020/016910
§ 371 (c)(1),
(2) Date: May 25, 2023

(87) PCT Pub. No.: WO2022/114261
PCT Pub. Date: Jun. 2, 2022

(65) Prior Publication Data
US 2024/0002439 A1  Jan. 4, 2024

(30) Foreign Application Priority Data

Nov. 25, 2020  (KR) ........................ 10-2020-0159849

(51) Int. Cl.
*C07K 7/06* (2006.01)
*A61K 8/64* (2006.01)
*A61Q 19/08* (2006.01)
*A61K 38/00* (2006.01)

(52) U.S. Cl.
CPC .................. *C07K 7/06* (2013.01); *A61K 8/64* (2013.01); *A61Q 19/08* (2013.01); *A61K 38/00* (2013.01); *A61K 2800/522* (2013.01)

(58) Field of Classification Search
CPC . C07K 7/06; A61K 8/64; A61K 38/00; A61K 2800/522; A61Q 19/08
See application file for complete search history.

(56) References Cited

U.S. PATENT DOCUMENTS

| 5,516,891 | A | 5/1996 | Siwruk |
| 5,578,566 | A | 11/1996 | Bottaro |
| 9,260,525 | B2 | 2/2016 | Chang |
| 10,544,203 | B2 | 1/2020 | Wang |
| 11,104,704 | B2 | 8/2021 | Chung |
| 11,433,013 | B2 | 9/2022 | Chung |
| 11,597,748 | B2 | 3/2023 | Chung |
| 2008/0064641 | A1 | 3/2008 | Rousselle |
| 2011/0059091 | A1 | 3/2011 | Chang |
| 2013/0142802 | A1 | 6/2013 | Chang |
| 2018/0104178 | A1 | 4/2018 | Portolan |
| 2019/0060216 | A1 | 2/2019 | Majeed |
| 2020/0377550 | A1 | 12/2020 | Chung |
| 2021/0205200 | A1 | 7/2021 | Chung |
| 2021/0371464 | A1 | 12/2021 | Chung |
| 2023/0227501 | A1 | 7/2023 | Chung |

FOREIGN PATENT DOCUMENTS

| CN | 110404051 A | 11/2019 |
| EA | 201992304 A1 | 2/2020 |
| EP | 3611182 A1 | 2/2020 |
| JP | 2016-088928 A | 5/2016 |
| KR | 10-1943083 B1 | 1/2019 |
| KR | 10-2065171 B1 | 1/2020 |
| KR | 10-2114275 B1 | 5/2020 |
| WO | 2012/021841 A2 | 2/2012 |
| WO | 2019/046508 A1 | 3/2019 |

OTHER PUBLICATIONS

International Search Report and Written Opinion issued in corresponding International Application No. PCT/KR2020/016910 dated Aug. 12, 2021, pp. 1-6, English Translation.
Merrifield, R.B., "Solid Phase Peptide Synthesis. I. The Synthesis of a Tetrapeptide" Journal of the American Chemical Society (Jan. 1963) pp. 2149-2154, vol. 85.
Kang, J-H, et al., "Particulate Matter and Skin" Korean J. Fam. Pract. (Jun. 2014) pp. 116-121, vol. 4, No. 2, English abstract.
Amann, T. et al., "Reduced Expression of Fibroblast Growth Factor Receptor 2IIIb in Hepatocellular Carcinoma Induces a More Aggressive Growth" The American Journal of Pathology (Mar. 2010) pp. 1433-1442, vol. 176, No. 3.
Petiot, A. et al., "A crucial role for Fgfr2-IIIb signalling in epidermal development and hair follicle patterning" Development (Aug. 2003) pp. 5493-5501, vol. 130, No. 22.
Russian Office Action issued in corresponding Russian Patent Application No. 2023114773, dated Nov. 30, 2023, with English translation.
Alvin, A W L et al., "Characterization of particulate matter binding peptides screened from phage display" Journal of Bioscience and Bioengineering (May 2017) pp. 621-624, vol. 123, No. 5.
Chen, Hsiao-Ling et al., "Kefir peptides alleviate particulate matter<4 μm (PM4. 0)-induced pulmonary inflammation by inhibiting the F-κB pathway using luciferase transgenic mice" Scientific Reports (Aug. 2019) pp. 1-13, vol. 9, No. 11529.
1st Office Action issued on Sep. 24, 2024 in corresponding Brazilian patent application No. 1120230101093.
Extended European Search Report issued by the European Patent Office on Apr. 8, 2024 in corresponding EP Patent Application No. 20963657.0.

*Primary Examiner* — Robert A Wax
*Assistant Examiner* — John W Lippert, III
(74) *Attorney, Agent, or Firm* — Carter, DeLuca & Farrell LLP

(57) ABSTRACT

The present application relates to a peptide having protective activity against cell damage caused by particulate matter, and to uses for the peptide.

18 Claims, 4 Drawing Sheets
Specification includes a Sequence Listing.

PEPTIDE HAVING PROTECTIVE ACTIVITY AGAINST CELL DAMAGE CAUSED BY PARTICULATE MATTER, AND USES FOR SAME

SEQUENCE LISTING

The application contains a Sequence Listing which has been submitted electronically in .txt format together with the International Application and is hereby incorporated by reference in its entirety. Said .txt copy, created on Nov. 26, 2020, is named "2020-OPA-4696PCT.TXT" and is 469 bytes in size. The sequence listing contained in this .txt file is part of the specification and is hereby incorporated by reference herein in its entirety.

TECHNICAL FIELD

The present application relates to a peptide having protective activity against cell damage caused by particulate matter, and to uses for the peptide.

BACKGROUND ART

Particulate matter refers to dust of small particles that are invisible. Particulate matter is an air pollutant including sulfur dioxide, nitrogen oxides, lead, ozone, carbon monoxide, etc., and is generated in automobiles, factories, cooking processes, etc. and suspended in the atmosphere for a long period of time. Particles having a diameter of 50 μm or less suspended in the atmosphere is referred to as total suspended particles (TSPs), and particles smaller than 10 μm among these TSPs are usually defined as particulate matter. Particulate matter is divided depending on the diameter of particles. The case of having a diameter of 10 μm or less is designated PM10, and the case of having a particle diameter of less than 2.5 μm is designated PM 2.5, and this is also called "fine particles" or "ultrafine particles."

Particulate matter contains carbon, organic hydrocarbons, nitrates, sulfates, and harmful metal components, and is known to directly cause respiratory diseases, cardiovascular diseases, eye diseases, cancer, skin diseases, headaches, etc. or exacerbate these diseases. In addition, since the particle size of particulate matter is about one-fifth of the pores of the skin, when the particulate matter penetrates into the skin, the protective membrane function of the outer layer of the skin is damaged and the skin becomes sensitive to irritation.

Polyaromatic hydrocarbons (PAHs) contained in the particulate matter enters the skin through hair follicles in the skin to increase melanocytes and pigmented macules, decrease collagen synthesis and increase collagen decomposition, thereby generating wrinkles and reducing elasticity, and promoting aging of the skin. The polyaromatic hydrocarbons can penetrate into cells, be bound to the aryl hydrocarbon receptor (AHR) that has penetrated into the cells, and translocated into the nucleus. The AHR translocated into the nucleus forms a complex AHR/ARNT with an AHR nuclear translocator (ARNT), and the complex "AHR/ARNT" binds to an AHR responsive element (AHRE), a dioxin responsive element (DRE), and an xenobiotic responsive element (XRE) sequence on DNA to generate a reactive oxygen species (ROS), or to generate toxic substances through enzymes such as CYP1A1, CYP1A2, and CYP1B1, thereby inducing cell damage, and to increase the expression of various inflammatory mediators, a microphthalmia-associated transcription factor (Mitf) which is a transcription factor related to melanin synthesis, and a matrix metalloproteases (MMPs), which is an enzyme related to wrinkle generation, thereby causing dermatitis, pigment hyperplasia (melasma, freckles, etc.), and wrinkles in the skin.

PRIOR ART DOCUMENTS

Patent Document

Korean Patent No. 10-2065171

DISCLOSURE OF THE INVENTION

Technical Problem

The present inventors have studied and made efforts to develop a peptide having activity capable of preventing damage to cells caused when cells of the body come into contact with particulate matter. As a result, the present invention was completed by experimentally proving that the peptide developed by the present inventors has a cell protective activity by inhibiting the activation of AHR induced by particulate matter and simultaneously inhibiting the activity of cytochrome P450 induced by the activation of AHR.

Accordingly, an aspect of the present invention provides a peptide having activity of effectively preventing damage to cells induced by particulate matter.

Another aspect of the present invention provides a composition for preventing cell damage, the composition including the peptide having the above-described activity as an active ingredient.

Still another aspect of the present invention provides a cosmetic composition for preventing skin cell damage, the composition including the peptide having the above-described activity as an active ingredient.

Yet another aspect of the present invention provides a pharmaceutical composition for treating or preventing a disease caused by contact with particulate matter, the composition including the peptide having the above-described activity as an active ingredient.

Technical Solution

In order to achieve the above objectives,

According to an aspect of the present invention, there is provided a peptide having activity of preventing cell damage caused by particulate matter, the peptide consisting of the amino acid sequence of SEQ ID NO: 1.

According to another aspect of the present invention, there is provided a composition for preventing cell damage caused by particulate matter, the composition including a peptide consisting of the amino acid sequence of SEQ ID NO: 1 as an active ingredient.

According to still another aspect of the present invention, there is provided a cosmetic composition for preventing skin cell damage caused by particulate matter, the cosmetic composition including a peptide consisting of the amino acid sequence of SEQ ID NO: 1 as an active ingredient.

According to yet another aspect of the present invention, there is provided a pharmaceutical composition for treating or preventing a disease caused by particulate matter, the pharmaceutical composition including a peptide consisting of the amino acid sequence of SEQ ID NO: 1 as an active ingredient.

Hereinafter, the present invention will be described in detail.

1. Peptide and Activity

According to an aspect of the present invention, there is provided a peptide consisting of the amino acid sequence of SEQ ID NO: 1.

As used herein, the term "peptide" refers to a linear molecule formed by amino acid residues linked together by peptide bonds.

The peptide consisting of the amino acid sequence of SEQ ID NO: 1 of the present invention may be used without modification, but on the other hand, the peptide may be a variant or fragment of an amino acid having a different sequence made by deletion, insertion, substitution, or a combination thereof of amino acid residues, within a range that does not affect the original activity of the peptide, such as the activity of protecting cell damage caused by particulate matter.

The peptide of the present invention may be modified by phosphorylation, sulfation, acrylation, glycosylation, methylation, famesylation, and the like within a range that does not change the activity of the peptide.

The peptide of the present invention includes a peptide including an amino acid sequence substantially identical to that of the peptide consisting of the amino acid sequence of SEQ ID NO: 1, and a variant thereof or an active fragment thereof. The peptide including a substantially identical amino acid sequence means a peptide including an amino acid sequence having at least 75%, for example, at least 80%, at least 90%, or at least 95% sequence identity to the amino acid sequence of SEQ ID NO: 1. The peptide may also include additional sequences such as targeting sequences, tags, labeled residues, or amino acids prepared for a particular purpose to increase the half-life or stability of the peptide.

The peptide of the present invention may have N-terminal and/or C-terminal modifications induced in order to select some regions of the amino acid sequence and increase the activity thereof. The stability of the peptide of the present invention may be significantly improved through the N-terminal and/or C-terminal modifications, and for example, the half-life of the peptide may be prolonged when the peptide is administered in vivo. The term "stability" of the peptide refers to not only stability in vivo for protecting the peptide of the present invention from the attack of in vivo protease, but also storage stability (e.g., storage stability at room temperature).

The N-terminal modification may be a bonding of a protecting group selected from the group consisting of an acetyl group, a fluorenylmethoxycarbonyl group, a formyl group, a palmitoyl group, a myristyl group, a stearyl group, and polyethylene glycol (PEG) to the N-terminus of the peptide.

The C-terminal modification may be a bonding of a hydroxyl group (—OH), an amino group (—NH$_2$), an azide —NHNH$_2$), and the like to the C-terminus of the peptide, but is not limited thereto.

The peptide of the present invention may be prepared by various methods widely known in the art to which the present invention belongs. For example, the peptides of the present invention may be prepared using chemical synthesis methods known in the art, particularly solid-phase synthesis techniques Merrifield, J. Amer. Chem. Soc. 85:2149-54 (1963); Stewart, et al., Solid Phase Peptide Synthesis, 2nd. ed., Pierce Chem. Co.: Rockford, 111(1984)) or a liquid-phase synthesis technique (U.S. Pat. No. 5,516,891).

The peptide of the present invention may effectively prevent cell damage caused by particulate matter.

The polyaromatic hydrocarbons (PAHs) contained in particulate matter may penetrate into cells, and the polyaromatic hydrocarbons that penetrate into the cells are bound to the aryl hydrocarbon receptor (AHR) and translocated into the nucleus. The AHR translocated into the nucleus forms a complex AHR/ARNT with an AHR nuclear translocator (ARNT), and the complex "AHR/ARNT" binds to an AHR responsive element (AHRE), a dioxin responsive element (DRE), and a xenobiotic responsive element (XRE) sequence present on DNA to generate a reactive oxygen species (ROS), or to increase the expression or activity of enzymes such as CYP1A1, CYP1A2, and CYP1B1, thereby generating toxic substances to induce cell damage and also increasing the expression of various inflammatory mediators.

The peptide of the present invention significantly inhibits the nuclear translocation of the aryl hydrocarbon receptor (AHR), which increases in cells due to contact with particulate matter, and cytochrome P450 activity, which increases as a result, thereby preventing cell damage caused by particulate matter.

2. Composition for Preventing Cell Damage

According to another aspect of the present invention, there is provided a composition for preventing cell damage caused by particulate matter, the composition including a peptide consisting of the amino acid sequence of SEQ ID NO: 1 as an active ingredient.

In an embodiment, the cell damage may be damage to skin cells, respiratory cells, or corneal cells.

In another embodiment, the peptide of the present invention may have activity to inhibit the activation of the aryl hydrocarbon receptor (AHR). The inhibition of the activation of AHR by the peptide may be inhibition of the translocation of AHR into the nucleus.

In another embodiment, the peptide of the present invention may have activity to inhibit the activity of cytochrome P450. The inhibition of the activity of cytochrome P450 by the peptide may be inhibition of the activation or expression of cytochrome P450.

In another embodiment, the particulate matter may include polycyclic aromatic hydrocarbons (PAHs).

According to another aspect of the present invention, there is provided a cosmetic composition for preventing skin cell damage caused by particulate matter, the cosmetic composition including a peptide consisting of the amino acid sequence of SEQ ID NO: 1 as an active ingredient.

In the present invention, damage to skin cells caused by particulate matter may include, for example, skin aging, an increase in skin wrinkles, damage to skin elasticity, damage to skin color, pigment hyperplasia, melasma, freckles, dry skin, skin inflammation, contact dermatitis, atopic dermatitis, or psoriasis.

The cosmetic composition may be a composition for use of ameliorating skin aging, an increase in skin wrinkles, damage to skin elasticity, damage to skin color, pigment hyperplasia, melasma, freckles, dry skin, skin inflammation, contact dermatitis, atopic dermatitis, or psoriasis.

The cosmetic composition of the present invention may include (i) a cosmetically effective amount of the peptide of the present invention described above; and (ii) a cosmetically acceptable carrier.

The term "cosmetically effective amount" refers to an amount sufficient for the composition of the present invention to achieve the effect of preventing skin cell damage caused by particulate matter.

The cosmetic composition of the present invention may be prepared in any formulation typically prepared in the art, and for example, may be formulated in solution, suspension, emulsion, paste, gel, cream, lotion, powder, soap, surfactant-containing cleanser, oil, powder foundation, emulsion foundation, wax foundation, and spray, but is not limited thereto. More specifically, it may be prepared in the formulation of skin softener, nutrition lotion, nutrition cream, massage cream, essence, eye cream, cleansing cream, cleansing foam, cleansing water, pack, spray, or powder.

When the formulation of the cosmetic composition of the present invention is paste, cream, or gel, animal oil, vegetable oil, wax, paraffin, starch, tragacanth, cellulose derivatives, polyethylene glycol, silicone, bentonite, silica, talc, or zinc oxide may be used as a carrier component. When the formulation of the cosmetic composition of the present invention is powder or spray, lactose, talc, silica, aluminum hydroxide, calcium silicate, or polyamide powder may be used as a carrier component, and particularly, when it is spray, a propellant such as chlorofluorohydrocarbon, propane/butane or dimethyl ether may be contained.

When the formulation of the cosmetic composition of the present invention is a solution or emulsion, a solvent, a solubilizer or an emulsifying agent is used as a carrier component, and for example, water, ethanol, isopropanol, ethyl carbonate, ethyl acetate, benzyl alcohol, benzyl benzoate, propylene glycol, 1,3-butyl glycol oil, glycerol aliphatic ester, polyethylene glycol, or fatty acid ester of sorbitan may be used.

When the formulation of the cosmetic composition of the present invention is suspension, a liquid diluent such as water, ethanol or propylene glycol, a suspending agent, such as ethoxylated isostearyl alcohol, polyoxyethylene sorbitol ester, polyoxyethylene sorbitan ester, microcrystalline cellulose, aluminum metahydroxide, bentonite, agar, tragacanth, or the like may be used as a carrier component.

When the formulation of the cosmetic composition of the present invention is a surfactant-containing cleanser, aliphatic alcohol sulfate, aliphatic alcohol ether sulfate, sulfosuccinic monoester, isethionate, imidazolium derivatives, methyl taurate, sarcosinate, fatty acid amide ether sulfate, alkyl amido betaine, aliphatic alcohol, fatty acid glyceride, fatty acid diethanolamide, vegetable oil, lanoline derivatives, ethoxylated glycerol fatty acid ester, or the like may be used as a carrier component.

The cosmetic composition of the present invention may include ingredients conventionally used in the cosmetic composition, in addition to the peptide as an active ingredient and the carrier component, and may include conventional additives, for example, antioxidants, stabilizers, solubilizers, vitamins, pigments, and fragrances.

According to yet another aspect of the present invention, there is provided a pharmaceutical composition for treating or preventing a disease caused by particulate matter, the pharmaceutical composition including a peptide consisting of the amino acid sequence of SEQ ID NO: 1 as an active ingredient.

In an embodiment, the peptide of the present invention may have activity to inhibit the activation of aryl hydrocarbon receptor (AHR). The inhibition of the activation of AHR by the peptide may be inhibition of the translocation of AHR into the nucleus.

In another embodiment, the peptide of the present invention may have activity to inhibit the activity of cytochrome P450. The inhibition of the activity of cytochrome P450 by the peptide may be inhibition of the activation or expression of cytochrome P450.

In another embodiment, the particulate matter may include polycyclic aromatic hydrocarbons (PAHs).

The term "prevention" refers to the inhibition of the occurrence of symptoms due to a disease caused by particulate matter or symptoms due to complications thereof, and the term "treatment" refers to the relief or elimination of symptoms due to a disease already caused by particulate matter or symptoms due to a complication of the disease.

The disease caused by particulate matter may be a disease selected from the group consisting of atopic dermatitis, contact dermatitis, seborrheic dermatitis, acne, xeroderma, psoriasis; allergic rhinitis, acute bronchitis, chronic bronchitis, emphysema, pulmonary function insufficiency, asthma, bronchiectasis, idiopathic pulmonary fibrosis, chronic obstructive pulmonary disease (COPD), cystic fibrosis, bronchiolitis, acute upper respiratory infections, pneumonia, nasosinusitis, pharyngitis, tonsillitis, laryngitis; xerophthalmia, allergic conjunctivitis, glaucoma, cataracts, macular degeneration, retinal hemorrhage, retinal detachment, retinitis pigmentosa, senile macular degeneration, diabetic retinopathy; cancer, immunotoxicity, peripheral nervous system damage, central nervous system damage, endocrinopathy, reproductive organ disorders, developmental disorders of infants and toddlers, anemia, arrhythmia, heart attack, angina, and myocardial infarction, but is not limited thereto.

The pharmaceutical composition of the present invention includes: (i) a therapeutically effective amount of the peptide of the present invention described above; and (ii) a pharmaceutically acceptable carrier.

The term "therapeutically effective amount" refers to an amount sufficient for the composition of the present invention to achieve the effect of treating or preventing a disease caused by particulate matter.

The pharmaceutically acceptable carrier is commonly used at the time of formulation, and examples thereof may include lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, mineral oil, and the like, but is not limited thereto. Suitable pharmaceutically acceptable carriers and formulations are described in detail in Remington's Pharmaceutical Sciences (19th ed., 1995).

The pharmaceutical composition of the present invention may be administered orally or parenterally, and in the case of parenteral administration, administration may be performed with intravenous injection, subcutaneous injection, intramuscular injection, intraperitoneal injection, transdermal administration, or the like.

A suitable dosage of the pharmaceutical composition of the present invention varies depending on factors such as the formulation method, administration method, the patient's age, body weight, sex, condition, diet, time of administration, route of administration, rate of excretion, and sensitivity of response, and an ordinary skilled physician can easily determine and prescribe an effective dosage for the desired treatment or prevention.

The daily dose of the pharmaceutical composition of the present invention is 0.001-10,000 mg/kg.

The pharmaceutical composition of the present invention may be prepared in a unit dose form by formulation using a pharmaceutically acceptable carrier and/or excipient or may be prepared by incorporating into a multi-dose container, according to a method which can easily be performed by those skilled in the art to which the present invention belongs. In this case, the formulation may be in the form of a solution, a suspension, or an emulsion in an oil or an aqueous medium, or may be in the form of an extract, a powder, a granule, a tablet, or a capsule, and may additionally include a dispersant or a stabilizer.

Advantageous Effects

The peptide of the present invention has outstanding activity of preventing cell damage caused by particulate matter, and can be used as an active substance in order to protect skin cells, respiratory cells, or corneal cells from particulate matter. In addition, the peptide of the present invention can be developed as a therapeutic agent for various diseases caused by particulate matter.

However, the effects of the present invention are not limited to the above-mentioned effects and other effects not mentioned will be clearly understood from the following description by a person skilled in the art.

MODE FOR CARRYING OUT THE INVENTION

Hereinafter, the present application will be described in detail with reference to examples. However, the following examples specifically illustrate the present application, and the contents of the present application are not limited by the following examples.

EXAMPLES

Preparation Example 1: Preparation of Peptide

Peptides having the amino acid sequence of SEQ ID NO: 1 shown in Table 1 below were synthesized using an automatic peptide synthesizer (Liberty, CEM Corporation, U.S.), and these synthesized peptides were purified by C18 reverse phase-high performance liquid chromatography (HPLC) (U-3000, Thermo fisher scientific, U.S.). Pursuit XRs C18 (250*4.65 mm 100 Å, Agilent, U.S.) was used as a column.

TABLE 1

| SEQ ID NO | Amino acid sequence of peptide |
|---|---|
| 1 | SSNAEVLALF |

Experimental Example 1: Nuclear Translocation Test of AHR

Polyaromatic hydrocarbons (PAHs) present in particulate matter act as a ligand of AHR, thereby promoting nuclear translocation of AHR when the PAHs penetrate into cells and binds to AHR. In order to confirm the effect of the synthesized peptide in inhibiting cell damage caused by particulate matter, an experiment was performed for proving whether the peptide inhibits the nuclear translocation of AHR observed at the time of ligand-AHR binding after the cells were treated with particulate matter.

HaCaT cells, which are human keratinocytes, were seeded into a 6-well plate at a density of $5 \times 10^5$ cells/well. After overnight incubation, the media were replaced with serum-free media. The keratinocytes, HaCaT were pretreated with the synthesized peptides for 1 hour at each concentration (20 μM, 100 μM, and 200 μM). Then, the cells were treated with 50 μg/cm$^2$ of urban particulate matter (Sigma, NIST1648A) for 1 hour. After keratinocytes were collected, cell nucleus extracts were prepared, and western blotting was performed. Western blotting was performed using anti-AHR antibodies (Cell Signaling Technology) according to a protocol known in the art.

Figure 1:
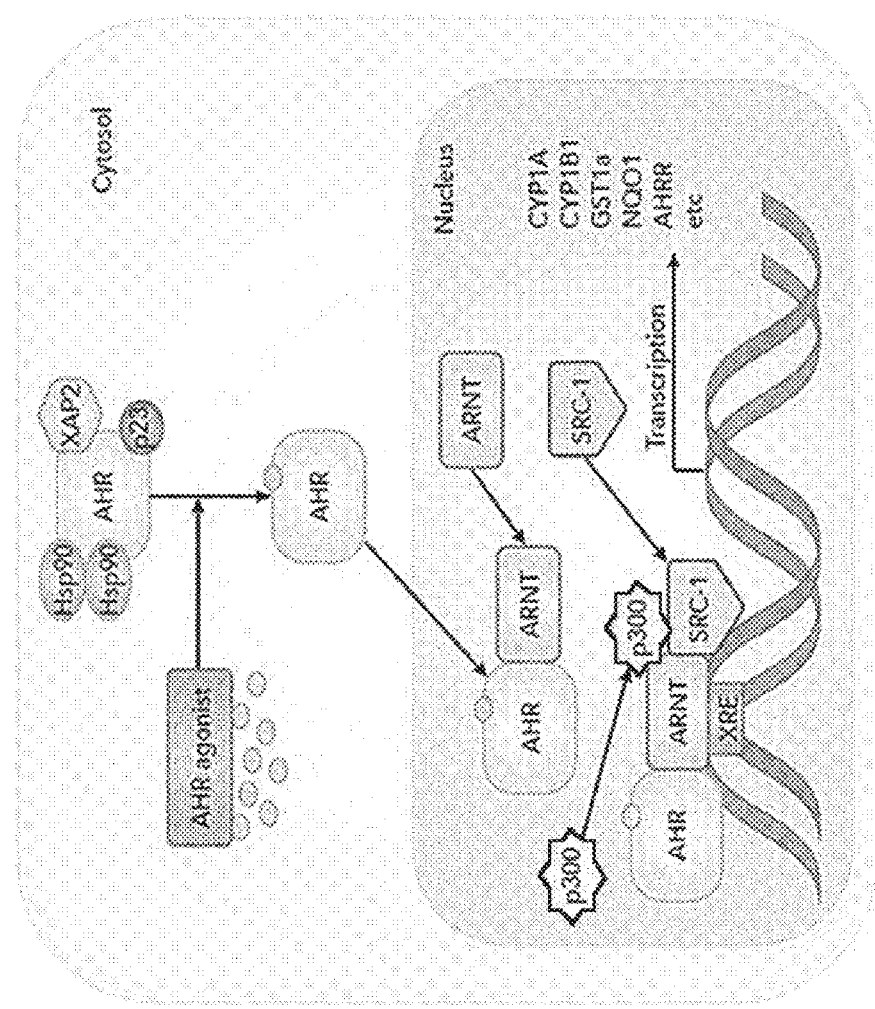
FIG. 1 is a schematic view illustrating signaling mechanisms mediated by the aryl hydrocarbon receptor (AHR).
Figure 2:
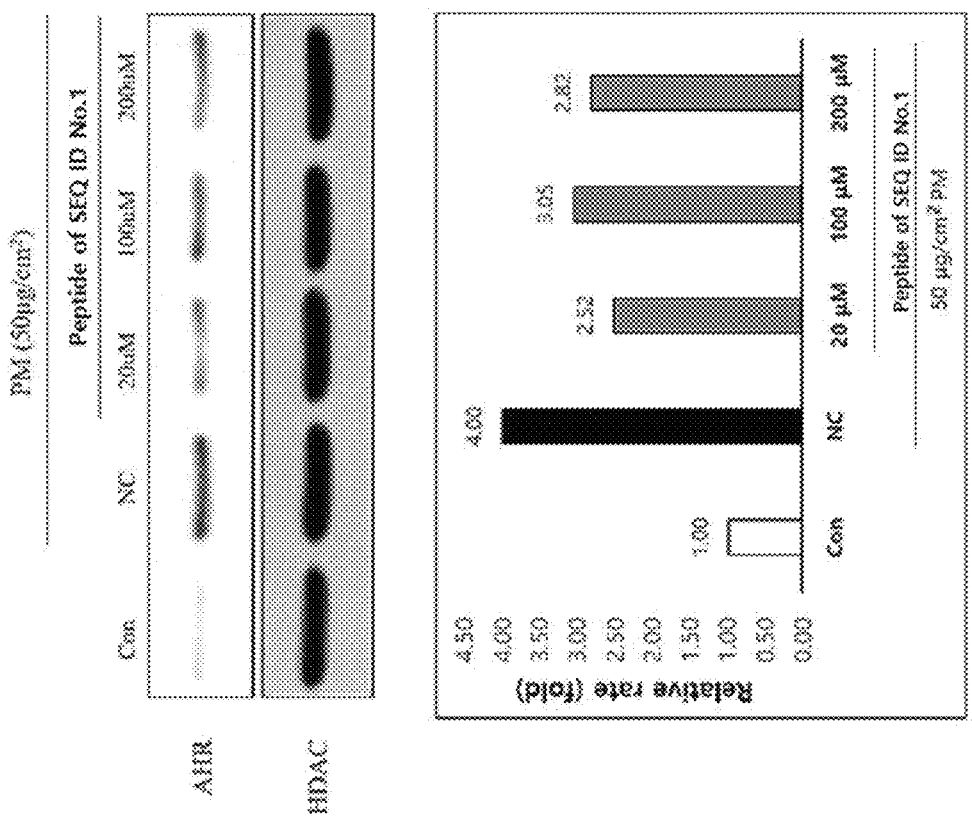
FIG. 2 shows a result of a Western blot experiment showing that an increase in the nuclear translocation of AHR induced by the treatment of particulate matter in human keratinocyte HaCaT is definitely reduced by the treatment of a peptide consisting of the amino acid sequence of SEQ ID NO: 1.

As a result of the experiment, as can be seen from the results of the western blotting shown in FIG. 2, it was confirmed that the nuclear translocation of AHR in the particulate matter-treated cells (NC) was rapidly increased compared to the control cells (Con) which were not treated with the particulate matter. In addition, it was confirmed that in the cells treated with the peptide of the amino acid sequence of SEQ ID NO: 1, the level of the nuclear translocation of AHR increased by the treatment of particulate matter was reduced definitely.

Experimental Example 2: Analysis of Cytochrome P450 Activity

When polyaromatic hydrocarbons (PAHs) present in particulate matter penetrate into cells and bind to AHR, it promotes nuclear translocation of AHR. It is known that the AHR translocated into the nucleus forms a complex AHR/ARNT with an AHR nuclear translocator (ARNT), and this complex act as a transcription factor to promote the expression of cytochrome P450 (CYPs). In order to confirm the effect of the synthesized peptide in inhibiting cell damage caused by particulate matter, an experiment was performed for confirming whether the peptide inhibits the activity of cytochrome P450 after the cells were treated with particulate matter.

First, HaCaT cells, which are human keratinocytes, were seeded into a 96-well plate at a density of $1 \times 10^4$ cells/well. After overnight incubation, the media were replaced with serum-free media. The keratinocytes, HaCaT were pretreated with the synthesized peptides for 1 hour at each concentration (20 μM, 100 μM, and 200 μM). Then, the cells were treated with 50 μg/cm² of urban particulate matter (Sigma, NIST1648A) for 24 hours. After the keratinocytes were collected, the activity of cytochrome P450 was measured using P450-Glo™ Assay kit (Promega).

Figure 3:
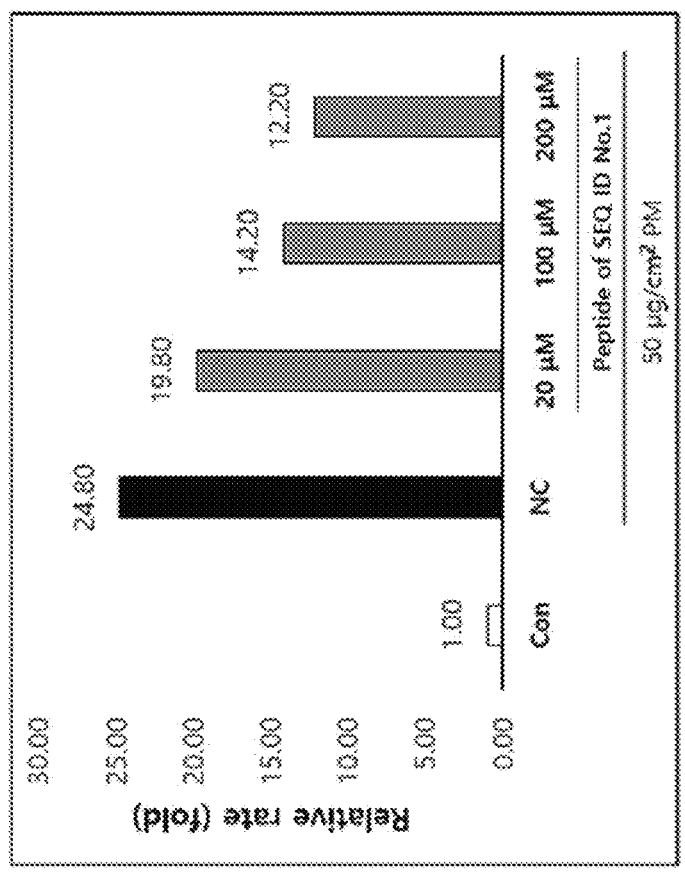
FIG. 3 shows a result of a P450 activity measurement experiment showing that an increase in activity of cytochrome P450 induced by the treatment of particulate matter in human keratinocyte HaCaT is reduced in a concentration-dependent manner by the treatment of a peptide consisting of the amino acid sequence of SEQ ID NO: 1.

As a result of the experiment, as can be seen from the results of measuring the activity of cytochrome P450 shown in FIG. 3, it was confirmed that the activity of cytochrome P450 was rapidly increased in the particulate matter-treated cells (NC) compared to the control cells (Con) which were not treated with the particulate matter. In addition, it was confirmed that in the cells treated with the peptide of the amino acid sequence of SEQ ID NO: 1, the activity of the cytochrome P450 increased by the treatment of particulate matter was reduced. In addition, the increase in the activity of cytochrome P450 by the treatment of particulate matter was reduced in a concentration dependent manner of the treated peptide when the cells were treated with the peptide.

In addition, in order to confirm whether the peptide can suppress respiratory damage caused by particulate matter, an experiment for measuring the activity of cytochrome P450 was also performed on A549 cells, which are human alveolar epithelial cells.

First, human alveolar epithelial cells, A549 cells were seeded into a 96-well plate at a density of 1.2×10⁴ cells/well. After overnight incubation, the media were replaced with serum-free media. The alveolar epithelial cells, A549 cells were pretreated with the synthesized peptides for 1 hour at each concentration (20 μM, 100 μM, and 200 μM). Then, the cells were treated with 50 μg/cm² of urban particulate matter (Sigma, NIST1648A) for 24 hours. After the treated cells were collected, the activity of cytochrome P450 was measured using P450-Glo™ Assay kit (Promega).

Figure 4:
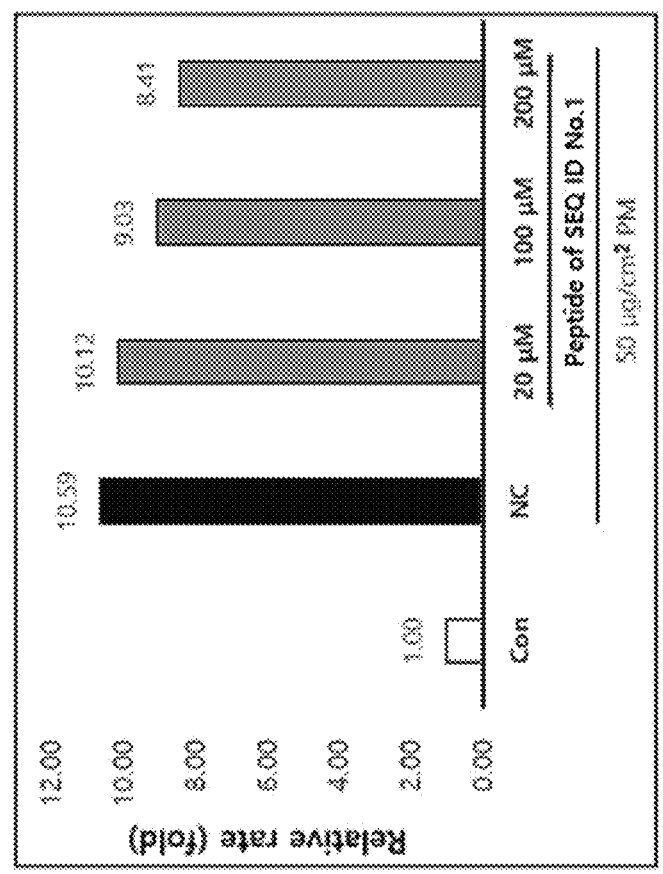
FIG. 4 shows a result of a P450 activity measurement experiment showing that an increase in activity of cytochrome P450 induced by the treatment of particulate matter in human alveolar epithelial cell A549 is reduced in a concentration-dependent manner by the treatment of a peptide consisting of the amino acid sequence of SEQ ID NO: 1.

As a result of the experiment, as can be seen from the results of measuring the activity of cytochrome P450 shown in FIG. 4, it was confirmed that the activity of cytochrome P450 was rapidly increased in the particulate matter-treated cells (NC) compared to the control cells (Con) which were not treated with particulate matter, and it was confirmed that the activity of cytochrome P450 increased by the treatment of particulate matter was reduced in the cells treated with the peptide of the amino acid sequence of SEQ ID NO: 1. In addition, the increase in the activity of cytochrome P450 by the treatment of particulate matter was reduced in a concentration dependent manner of the treated peptide when the cells were treated with the peptide.

Although the representative embodiments of the present application have been exemplarily described, the scope of the present application is not limited to the specific embodiments as described above, and a person skilled in the art can change the present application within the scope described in the claims of the present application.

SEQUENCE LIST FREE TEXT

SEQ ID NO: 1: Ser Ser Asn Ala Glu Val Leu Ala Leu Phe

The invention claimed is:

1. A peptide consisting of the amino acid sequence of SEQ ID NO: 1.

2. A composition for preventing cell damage caused by particulate matter, the composition comprising a peptide consisting of the amino acid sequence of SEQ ID NO: 1 as an active ingredient.

3. The composition of claim 2, wherein the cell damage is damage to skin cells, respiratory cells, or corneal cells.

4. The composition of claim 2, wherein the peptide inhibits the activation of the aryl hydrocarbon receptor (AHR).

5. The composition of claim 2, wherein the peptide inhibits the activity of cytochrome P450.

6. The composition of claim 2, wherein the particulate matter comprises polycyclic aromatic hydrocarbons (PAHs).

7. A cosmetic composition for preventing skin cell damage caused by particulate matter, the cosmetic composition comprising a peptide consisting of the amino acid sequence of SEQ ID NO: 1 as an active ingredient.

8. The cosmetic composition of claim 7, wherein the skin cell damage includes skin aging, an increase in skin wrinkles, damage to skin elasticity, damage to skin color, pigment hyperplasia, melasma, freckles, dry skin, skin inflammation, contact dermatitis, atopic dermatitis, or psoriasis.

9. The cosmetic composition of claim 7, wherein the composition has at least one formulation selected from the group consisting of solution, suspension, emulsion, gel, lotion, essence, cream, powder, soap, shampoo, rinse, mask pack, surfactant-containing cleanser, cleansing foam, cleansing water, oil, liquid foundation, cream foundation, and spray.

10. A pharmaceutical composition for treating a disease caused by particulate matter, the pharmaceutical composition comprising a peptide consisting of the amino acid sequence of SEQ ID NO: 1 as an active ingredient.

11. The pharmaceutical composition of claim 10, wherein the disease caused by particulate matter is a disease selected from the group consisting of atopic dermatitis, contact dermatitis, seborrheic dermatitis, acne, xeroderma, psoriasis; allergic rhinitis, acute bronchitis, chronic bronchitis, emphysema, pulmonary function insufficiency, asthma, bronchiectasis, idiopathic pulmonary fibrosis, chronic obstructive pulmonary disease, cystic fibrosis, bronchiolitis, acute upper respiratory infections, pneumonia, nasosinusitis, pharyngitis, tonsillitis, laryngitis; xerophthalmia, allergic conjunctivitis, glaucoma, cataracts, macular degeneration, retinal hemorrhage, retinal detachment, retinits pigmentosa, senile macular degeneration, diabetic retinopathy; cancer, immunotoxicity, peripheral nervous system damage, central nervous system damage, endocrinopathy, reproductive organ disorders, developmental disorders of infants and toddlers, anemia, arrhythmia, heart attack, angina, and myocardial infarction.

12. The pharmaceutical composition of claim 10, wherein the peptide inhibits the activation of the aryl hydrocarbon receptor (AHR).

13. The pharmaceutical composition of claim 10, wherein the peptide inhibits the activity of cytochrome P450.

14. The pharmaceutical composition of claim 10, wherein the particulate matter comprises polycyclic aromatic hydrocarbons (PAHs).

15. A method of treating cell damage caused by particulate matter in a subject in need thereof, the method comprising administering to the subject a composition comprising an effective amount of the peptide of claim 1.

16. A method of treating skin cell damage caused by particulate matter in a subject in need thereof, the method comprising administering to the subject a cosmetic composition comprising an effective amount of the peptide of claim 1.

17. A method of ameliorating skin aging, an increase in skin wrinkles, damage to skin elasticity, damage to skin color, pigment hyperplasia, melasma, freckles, dry skin, skin inflammation, contact dermatitis, atopic dermatitis, or psoriasis in a subject in need thereof, the method comprising administering to the subject a cosmetic composition comprising an effective amount of the peptide of claim 1.

18. A method of treating a disease caused by particulate matter in a subject in need thereof, the method comprising administering to the subject a pharmaceutical composition comprising an effective amount of the peptide of claim 1.

* * * * *

SEQUENCE LISTING

```
<160> NUMBER OF SEQ ID NOS: 1

<210> SEQ ID NO 1
<211> LENGTH: 10
<212> TYPE: PRT
<213> ORGANISM: Artificial Sequence
<220> FEATURE:
<223> OTHER INFORMATION: Artificial Peptide

<400> SEQUENCE: 1

Ser Ser Asn Ala Glu Val Leu Ala Leu Phe
1               5                   10
```